(12) United States Patent
Levine et al.

(10) Patent No.: US 8,292,884 B2
(45) Date of Patent: Oct. 23, 2012

(54) CARDIAC DEVICES AND METHODS FOR MINIMALLY INVASIVE REPAIR OF ISCHEMIC MITRAL REGURGITATION

(76) Inventors: Robert A. Levine, Brookline, MA (US); Emmanuel Messas, Paris (FR)

( * ) Notice: Subject to any disclaimer, the term of this patent is extended or adjusted under 35 U.S.C. 154(b) by 665 days.

(21) Appl. No.: 10/523,096

(22) PCT Filed: Aug. 1, 2003

(86) PCT No.: PCT/US03/24367
§ 371 (c)(1), (2), (4) Date: Aug. 31, 2005

(87) PCT Pub. No.: WO2004/012583
PCT Pub. Date: Feb. 12, 2004

(65) Prior Publication Data
US 2006/0095025 A1    May 4, 2006

Related U.S. Application Data

(60) Provisional application No. 60/400,151, filed on Aug. 1, 2002.

(51) Int. Cl.
*A61B 17/32* (2006.01)
(52) U.S. Cl. .................. 606/41; 606/42; 606/52
(58) Field of Classification Search .......... 128/898; 606/167–185; 600/564
See application file for complete search history.

(56) References Cited

U.S. PATENT DOCUMENTS

| | | | | |
|---|---|---|---|---|
| 4,960,424 A | * | 10/1990 | Grooters ............... | 128/898 |
| 5,052,402 A | * | 10/1991 | Bencini et al. ........ | 600/564 |
| 5,507,795 A | * | 4/1996 | Chiang et al. ......... | 606/167 |
| 5,558,644 A | * | 9/1996 | Boyd et al. ............ | 604/102.02 |
| 5,607,389 A | * | 3/1997 | Edwards et al. ...... | 604/22 |
| 5,626,578 A | * | 5/1997 | Tihon ................... | 606/48 |
| 5,643,248 A | * | 7/1997 | Yoon .................... | 606/1 |
| 5,779,715 A | * | 7/1998 | Tu ........................ | 606/108 |
| 5,800,450 A | * | 9/1998 | Lary et al. ............. | 606/180 |
| 5,853,368 A | | 12/1998 | Solomon et al. | |
| 5,868,768 A | * | 2/1999 | Wicherski et al. .... | 606/159 |
| 5,906,630 A | * | 5/1999 | Anderhub et al. .... | 606/205 |
| 5,957,863 A | * | 9/1999 | Koblish et al. ....... | 600/567 |
| 5,972,030 A | * | 10/1999 | Garrison et al. ...... | 623/2.11 |
| 6,027,514 A | | 2/2000 | Stine et al. | |

(Continued)

FOREIGN PATENT DOCUMENTS

JP    H05-184535    7/1993

(Continued)

OTHER PUBLICATIONS

Robert A. Levine et al., "Ischemic Mitral Regurgitation on the Threshold of a Solution from Paradoxes to Unifying Concepts", Contemporary Reviews in Cardiovascular Medicine, 2005; 112, pp. 745-758.

(Continued)

*Primary Examiner* — Aaron Roane
(74) *Attorney, Agent, or Firm* — Dorsey & Whitney LLP

(57) ABSTRACT

Novel apparatus and minimally invasive methods to treat atrioventricular valve regurgitation that is a result of tethering of chordae attaching atrioventricular valve leaflets to muscles of the heart, such as papillary muscles and muscles in the heart wall, thereby restricting the closure of the leaflets. Catheter embodiments for delivering and positioning chordal severing and elongating instruments are described.

34 Claims, 10 Drawing Sheets

U.S. PATENT DOCUMENTS

| | | | |
|---|---|---|---|
| 6,080,175 A | 6/2000 | Hogendijk | |
| 6,113,395 A * | 9/2000 | Hon | 434/262 |
| 6,129,758 A | 10/2000 | Love | |
| 6,165,183 A | 12/2000 | Kuehn et al. | |
| 6,251,128 B1 * | 6/2001 | Knopp et al. | 607/100 |
| 6,269,819 B1 | 8/2001 | Oz et al. | |
| 6,283,127 B1 * | 9/2001 | Sterman et al. | 128/898 |
| 6,312,447 B1 | 11/2001 | Grimes | |
| 6,355,030 B1 | 3/2002 | Aldrich | |
| 6,402,679 B1 | 6/2002 | Mortier et al. | |
| 6,432,039 B1 | 8/2002 | Wardle | |
| 6,451,054 B1 * | 9/2002 | Stevens | 623/2.11 |
| 6,461,366 B1 | 10/2002 | Seguin | |
| 6,537,314 B2 * | 3/2003 | Langberg et al. | 623/2.36 |
| 6,540,666 B1 | 4/2003 | Chekanov | |
| 6,575,971 B2 | 6/2003 | Hauck et al. | |
| 6,626,899 B2 * | 9/2003 | Houser et al. | 606/14 |
| 6,626,930 B1 | 9/2003 | Allen et al. | |
| 6,629,534 B1 * | 10/2003 | St. Goar et al. | 128/898 |
| 6,651,672 B2 * | 11/2003 | Roth | 128/898 |
| 6,695,866 B1 | 2/2004 | Kuehn et al. | |
| 6,752,813 B2 | 6/2004 | Goldfarb et al. | |
| 6,770,083 B2 | 8/2004 | Seguin | |
| 2002/0013571 A1 | 1/2002 | Goldfarb et al. | |
| 2002/0029060 A1 | 3/2002 | Hogendijk | |
| 2002/0100485 A1 * | 8/2002 | Stevens et al. | 128/898 |
| 2002/0161378 A1 | 10/2002 | Dowing | |
| 2002/0173811 A1 * | 11/2002 | Tu et al. | 606/159 |
| 2003/0018358 A1 * | 1/2003 | Saadat | 606/232 |
| 2003/0105519 A1 * | 6/2003 | Fasol et al. | 623/2.1 |
| 2003/0120341 A1 | 6/2003 | Shennib et al. | |
| 2003/0145865 A1 * | 8/2003 | Sterman et al. | 128/898 |
| 2004/0034380 A1 * | 2/2004 | Woolfson et al. | 606/170 |

FOREIGN PATENT DOCUMENTS

| | | |
|---|---|---|
| JP | H08-38503 | 2/1996 |
| JP | H10-192280 | 7/1998 |
| JP | 2001-505460 | 4/2001 |
| JP | 2001-137251 | 5/2001 |
| JP | 2001-521795 | 11/2001 |
| JP | 2001-340285 | 12/2001 |
| WO | 9635469 | 11/1996 |
| WO | WO 98/24372 | 6/1998 |
| WO | 9913777 | 3/1999 |
| WO | WO 99/22797 | 5/1999 |
| WO | WO 99/44524 | 9/1999 |
| WO | WO 00/33724 | 6/2000 |
| WO | 0060995 | 10/2000 |
| WO | WO 00/60995 | 10/2000 |
| WO | WO 01/00114 | 1/2001 |
| WO | WO 01/03723 | 1/2001 |
| WO | 0128432 | 4/2001 |
| WO | WO 02/053206 | 7/2002 |
| WO | 2004002364 | 1/2004 |
| WO | 2004014282 | 2/2004 |

OTHER PUBLICATIONS

Judy Hung et al., "Reverse Ventricular Remodeling Reduces Ischemic Mitral Regurgitation Echo-Guided Device Application in the Beating Heart", Circulation, Nov. 12, 2002, pp. 2594-2600.

Judy Hung et al., "Mechanism of Recurrent Ischemic Mitral Regurgitation After Annuloplasty continued LV remodeling as a moving target", Circulation, Sep. 14, 2004, pp. 85-90.

Emmanuel Messas et al., "Chordal Cutting a New Therapeutic Approach for Ischemic Mitral Regurgitation", Ischemic Mitral Regurgitation, Jul. 2001, pp. 1958-1963.

Emmanuel Messas et al., "Efficacy of Chordal Cutting to Relieve Chronic Persistent Ischemic Mitral Regurgitation", Circulation, Sep. 9, 2003, pp. 111-115.

International Search Report for International application No. PCT/US03/24367.

European Search Report for European Patent Application No. EP 03 76 7158.

Office Action for U.S. Appl. No. 10/640,974.

International Search Report for International Application No. PCT/US03/20450.

Japanese Office Action mailed Apr. 4, 2009 for Japanese Patent Application No. 2004-526409.

Japanese Office Action mailed Mar. 30, 2010 for Japanese Patent Application No. 2004-526409.

* cited by examiner

Fig. 3A
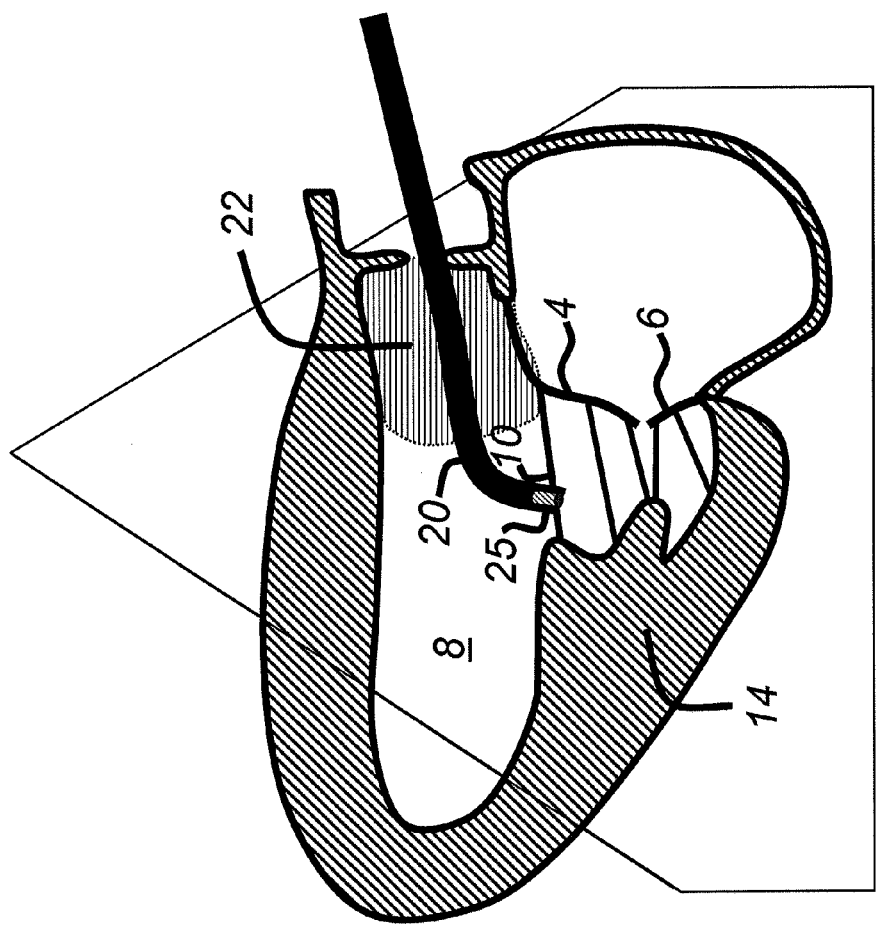
Fig. 3B
Fig. 3

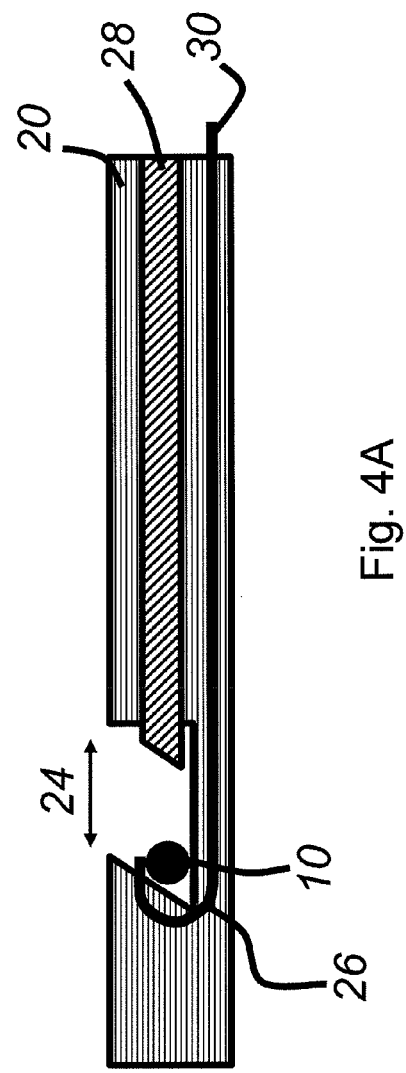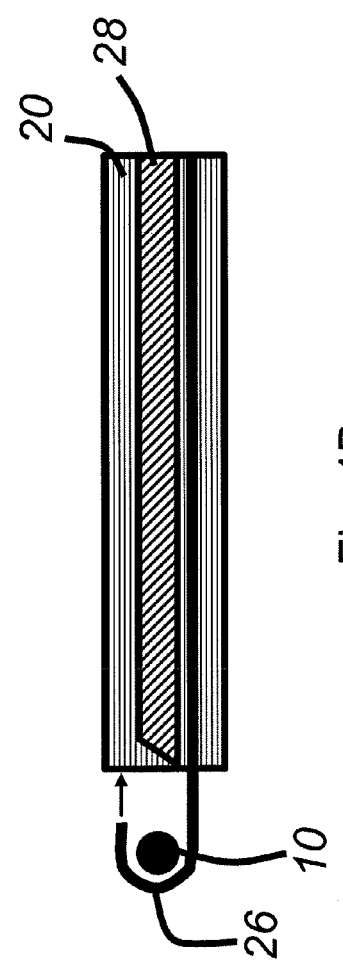
Fig. 4A
Fig. 4B

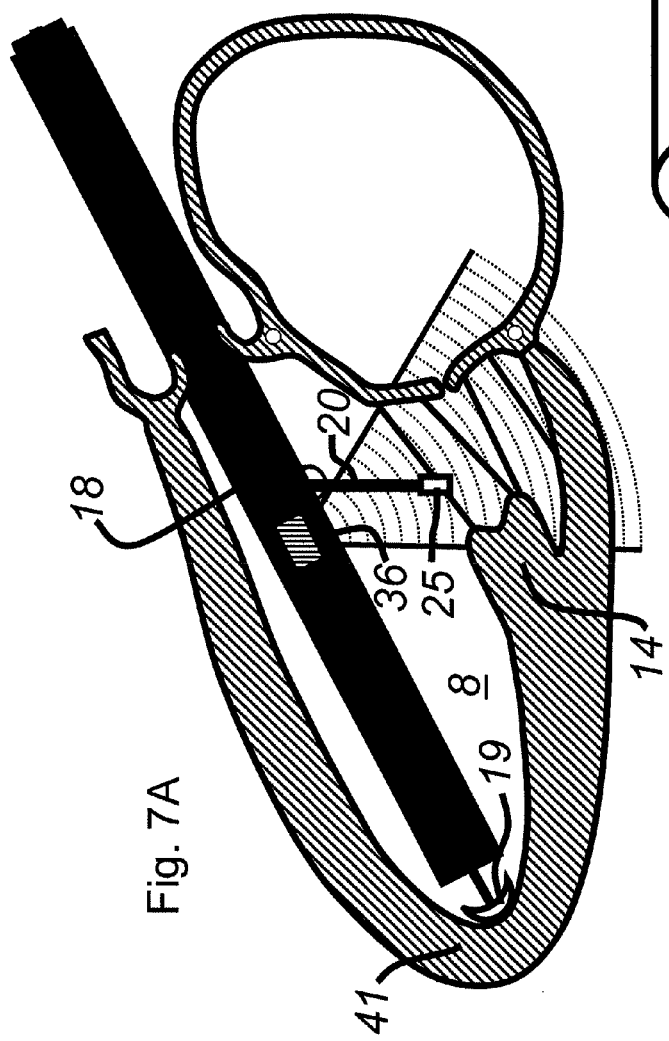
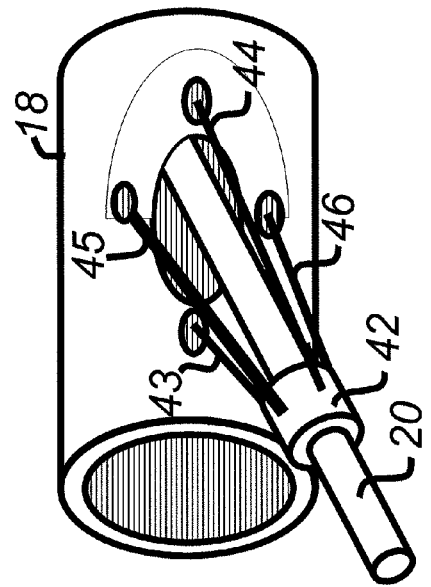
Fig. 7A
Fig. 7B

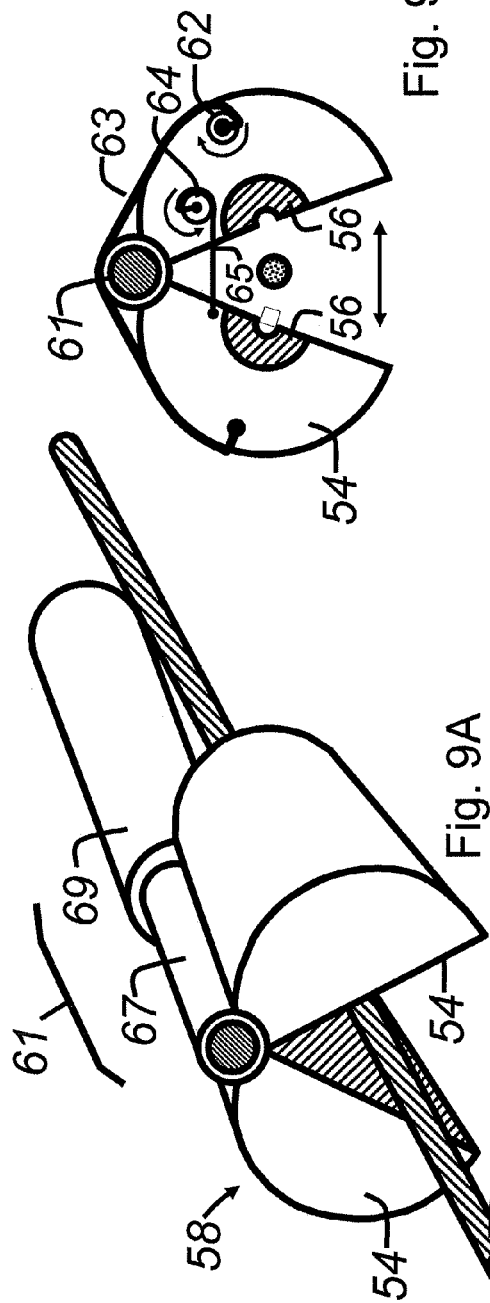
Fig. 9A
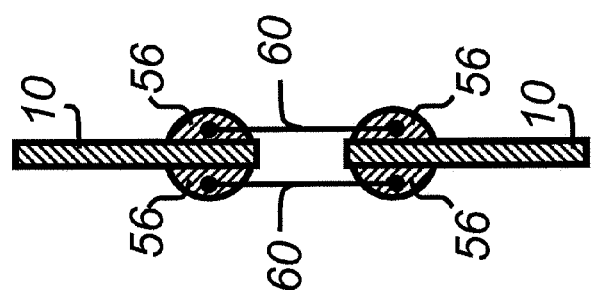
Fig. 9B
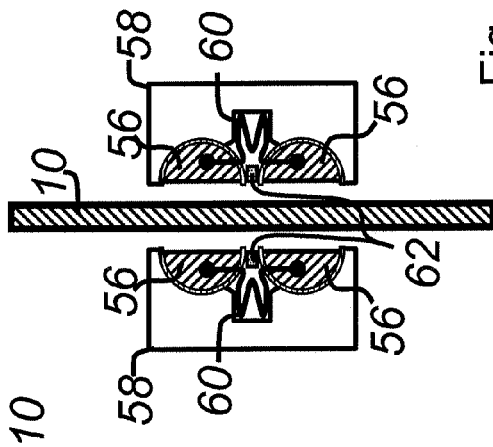
Fig. 9C
Fig. 9D

CARDIAC DEVICES AND METHODS FOR MINIMALLY INVASIVE REPAIR OF ISCHEMIC MITRAL REGURGITATION

CROSS-REFERENCE TO RELATED APPLICATIONS

This application claims priority of International Application No. PCT/US2003/024367 filed on Aug. 1, 2003, and U.S. Provisional Application No. 60/400,151 filed on Aug. 1, 2002, the entirety of which are incorporated herein by reference.

FIELD OF THE INVENTION

The present invention relates generally to devices (i.e., articles of manufacture, apparatus, systems, instruments) and methods for treating heart disease and, in particular, to devices and methods for minimally invasive repair of mitral valve regurgitation occurring in the context of cardiac pump dysfunction.

BACKGROUND OF THE INVENTION

With reference to FIG. 1A, the heart's mitral valve 2, comprised of an anterior leaflet 4 and a posterior leaflet 6, is the inlet valve to the main heart pumping chamber (left ventricle 8), and is forced to close when the ventricle contracts, preventing backward flow of blood. To ensure that this valve does not prolapse backward when the heart contracts, the leaflets 4,6 are restrained by a network of tendinous chords 10 that are anchored to the posterior wall 12 of the heart to prevent such prolapse. Two papillary muscles 14 (one shown in the figure) serve as anchoring structures.

Patients with coronary artery disease and insufficient blood supply to the heart muscle (e.g., ischemic heart disease and heart attack) often develop regurgitation of the mitral valve 2, i.e. leakage or back-ward flow of blood such as indicated by arrow 16 in FIG. 1B. Regurgitation also occurs in patients with weakened heart muscle (cardiomyopathy) and/or global contractile dysfunction. Such regurgitation limits exercise capacity by reducing forward blood flow to the body and overloading the lungs, causing fatigue and shortness of breath as cardinal manifestations of heart failure; if unrepaired, regurgitation also doubles the late mortality after heart attack and coronary artery bypass surgery.

Such functional mitral regurgitation (MR) fundamentally relates to dysfunction of the ventricle 8, since the leaflets 4,6 are structurally normal. Damaged heart muscle bulges or expands outward, as indicated, for example, in the direction indicated by arrow 20. When this process affects the wall segment 5 underlying the papillary muscles 14, the tethered leaflets 4,6 are displaced as well, restricting their ability to close effectively, so that regurgitation results.

Current therapy for functional MR involves reducing the size of the mitral annulus, the structure to which the mitral leaflets insert. Annular reduction, however, is often ineffective because it does not correct the fundamental heart wall deformation, so the mitral valve leaflets remain tethered. Heart wall deformation or remodeling may also progress over time, so that even with initial success in reducing regurgitation, it often recurs after annular reduction therapy. Moreover, in current practice, annular reduction procedures require putting patients on cardiopulmonary bypass (stopping the heart and opening it to insert the ring while using an artificial pump to bypass the heart and lungs), which itself conveys additional risk, deterring surgeons from performing this procedure.

Another solution is to re-shape the damaged ventricle underlying the papillary muscles by muscle excision, plication surgery, or an external compressing device. Such techniques, however, require open-chest exposure of the heart and often extensive surgical manipulation. There have been some efforts in manipulating chordal geometry to treat prolapse, but these have focused on increasing the tension on the chords through grabbing groups of chords or heat application. These methods attempt to shorten chord length, an opposite goal of the present invention.

Thus, what is needed is a minimally invasive therapy for ischemic MR that may not require cardiopulmonary bypass.

SUMMARY OF THE INVENTION

The present invention provides novel devices and minimally invasive methods to treat atrioventricular valve regurgitation that is a result of tethering of chordae attaching atrioventricular valve leaflets to muscles of the heart, such as papillary muscles and muscles in the heart wall, thereby restricting the closure of the leaflets. Use of a novel percutaneous catheter and other novel devices disclosed herein enables therapeutic maneuvers that do not require opening the chest or heart, however the present invention is not limited to percutaneous approaches. The devices and methods provided herein modify the connection between the valve leaflets and the heart wall. In the description that follows, several specific references to adjusting anterior leaflets of mitral valves appear that are meant in no way to be limiting. It will be readily appreciated that the present invention may additionally be effectively applied to chords of the tricuspid valve and/or to basal and mural chords of the posterior leaflet. As used herein, the term "basal" is understood to mean chords inserting near the basal attachment of a leaflet to the heart (i.e., a hinging region) or onto the body of a leaflet near this region, away from the free edge or margin of the valve.

With reference to FIG. 1B, there are several critically positioned chords 11 (one shown in the figure) attached to the base (insertion) of the anterior mitral leaflet 4 that deform that leaflet to the greatest extent. An effective seal requires the leaflets 4,6 to contact one another over an extended surface. However, the increased tension on the chords caused by deformation of the heart wall 12 creates a bend in the anterior leaflet so that it can barely meet the posterior leaflet at its tip.

In a first embodiment, the present invention provides instruments for and methods of severing one or more of these basal (non-marginal) chords 11 (as shown in FIG. 1C) to eliminate the bend in the anterior leaflet 4 and allow the leaflets 4,6 to assume a more normal configuration, with more effective closure. At the same time, the intact chords to the margins or free edges of the leaflets continue to prevent prolapse. This approach, preferably, but not exclusively, involves symmetrically cutting the two chords 11,13 of the anterior leaflet 4 that are closest to the central axis 15 of the ventricle, as shown in FIG. 2. These chords may or may not be symmetrically positioned.

The severing process, as stated, is performed utilizing a novel cutting instrument that is positioned in a minimally invasive manner near the chord (or chords) to be severed. This may require use of a positioning catheter through which the cutting device is advanced. In various embodiments, the cutting instrument is advanced retrograde via the arterial system into the left ventricle, through the venous system and right atrium into the left atrium across the atrial septum, directly through the wall of the heart, or percutaneously through a small incision in the chest wall and pericardium.

The positioning catheter includes an opening through which the cutting instrument severs the selected chord. For example, the end of the catheter may be open, allowing extension and retraction of cutting instruments, or a notch may be formed in the catheter near the end, allowing the cutting instrument to access the chord. In preferred embodiments, the notch is dimensioned and shaped so as to enable capture of a portion of the chord. In some configurations, the portion of chord may be grasped prior to severing by components of the cutting instrument. Several embodiments of tools and methods for grasping and/or pinioning a portion of the chord to be severed are described below.

In certain embodiments, the end of the catheter is steerable and/or has a pre-formed bend, such as, for example, might be necessary to reach chords of the posterior leaflet. Any known approach to steering the tip of a catheter may be employed, such as, but not limited to, coaxial steering wires.

The severing of the selected chord is achieved by different modalities in various embodiments. Options include, for example, a cutting blade having a diameter near or greater than the diameter of the chord to be cut, or direction of ablative optical or radiofrequency energy to the cutting site(s).

In another embodiment of the present invention, the positioning catheter is advanced to a position proximate the chord to be severed through an introducer catheter. The introducer catheter preferably includes a means for temporarily stabilizing the position of the positioning catheter, and thus the cutting instrument near the chord to be cut.

External or internal cardiac imaging of the region of the chord and valve regurgitation may be employed to facilitate proper positioning of the cutting instrument and/or monitoring of effectiveness of the procedure. This imaging can alternatively be achieved through the use of ultrasound, magnetic resonance or fiber optics.

In yet another embodiment, the present invention provides devices and methods of treating atrioventricular valve regurgitation that involve elongating the one or more chords causing leaflet tethering. The embodiments described below involve attaching two nodes to different points along the length of chord to be elongated, and severing the chord between them. The nodes are connected by an adjustable or predetermined length of artificial chordal material that effectively replaces the severed section of actual chord between the nodes, thereby elongating the chord and the distance between the tethered leaflet and the papillary or ventricular wall muscle to which the leaflet is tethered. Several embodiments of an instrument for positioning the nodes and severing the chord are described below.

For a better understanding of the present invention, together with other and further objects thereof, reference is made to the accompanying drawings and detailed description.

BRIEF DESCRIPTION OF THE DRAWING

The advantages of the present invention will be apparent in the following detailed description of the illustrative embodiments thereof, which is to be read in connection with the accompanying drawing, wherein:

FIG. 3A is a photographic reproduction of an ultrasound image of a region of a heart including the mitral valve and surrounding structures;

FIG. 3B is a an illustration of a cross-sectional view of a heart into which has been inserted a positioning catheter delivering a chordal severing instrument;

FIGS. 4A,4B are schematic illustrations of side views of the end of the positioning catheter wherein are disposed grasping and cutting mechanisms;

FIG. 7A is a schematic illustration of a side view of a heart into which has been inserted introducer and positioning catheters for stably positioning a chordal severing instrument;

FIG. 7B is a schematic illustration of a port in an introducer catheter through which a positioning catheter is extended, and a steering mechanism for the positioning catheter;

FIGS. 9A-9G are schematic illustrations of various views of a chordal elongation device.

DETAILED DESCRIPTION OF PREFERRED EMBODIMENTS OF THE INVENTION

Figure 1:
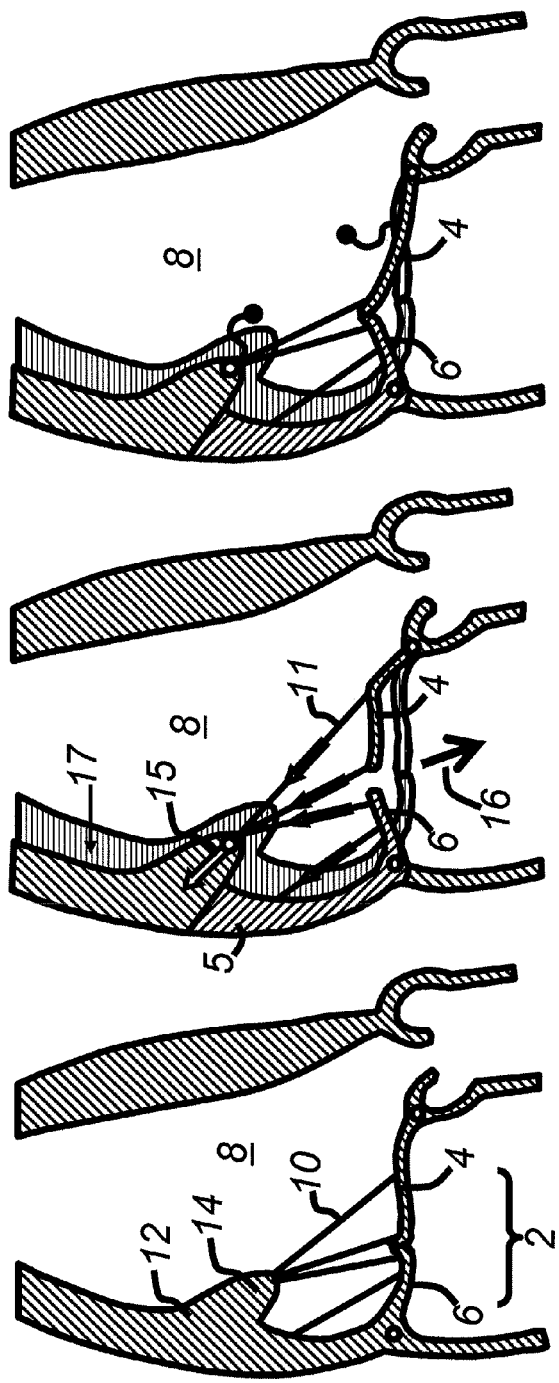
FIG. 1A is an illustration of a cross-sectional view of a heart having normal mitral valve geometry.
FIG. 1B is an illustration of a cross-sectional view of a heart experiencing mitral valve regurgitation as a result of leaflet tethering.
FIG. 1C is an illustration of a cross-sectional view of a heart having restored leaflet coaptation as a result of chordal severing.
Figure 2:
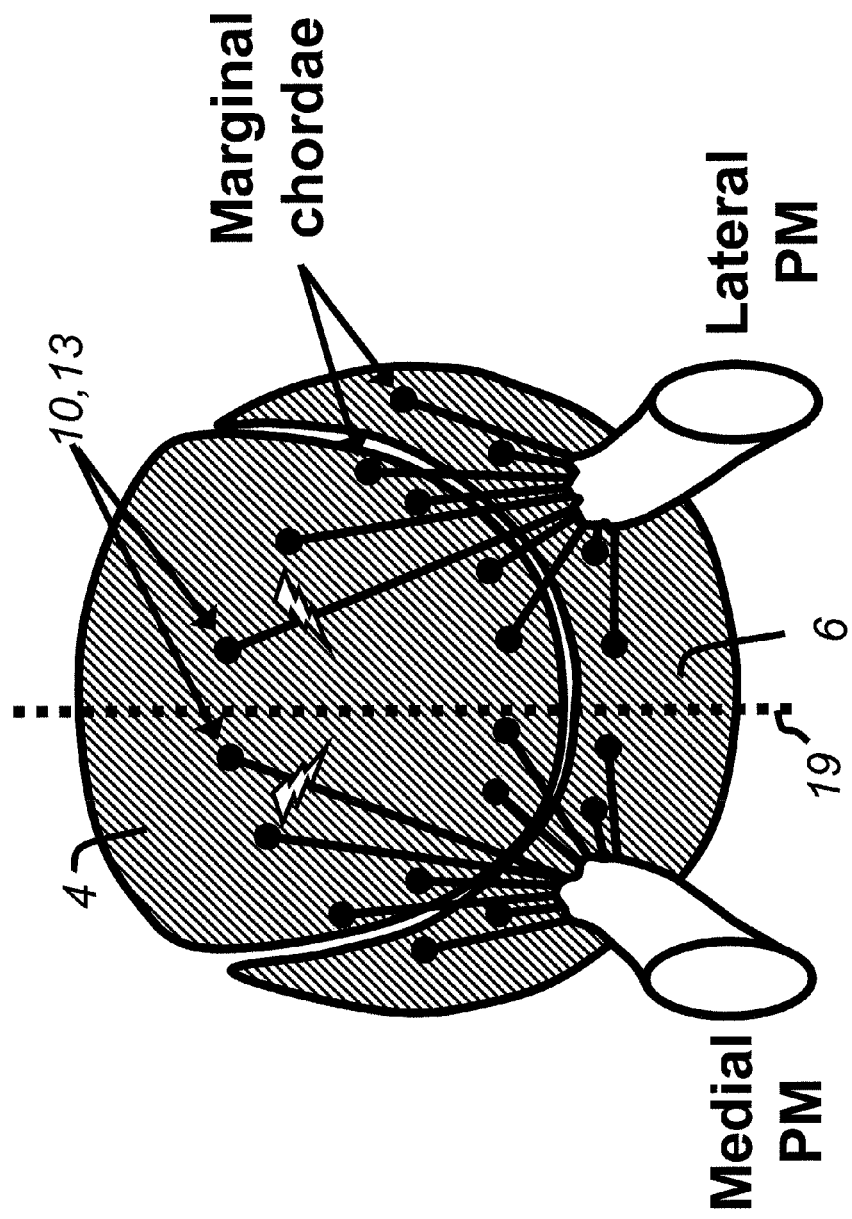
FIG. 2 is an illustration of a mitral valve showing basal and marginal chordae attached between the papillary muscles and anterior and posterior leaflets.

Preferred embodiments of the present invention will now be described with reference to the several figures of the drawing.

As shown in FIG. 3B, the present invention involves a percutaneous catheter 20 that may be advanced retrograde from the aorta into the outflow tract 22 of the left ventricle. The catheter is inserted using a standard guidewire approach (Seldinger technique), typically from the femoral artery in the groin. The catheter has a pre-formed or maneuverable bend that brings a cutting instrument 25 near a chord to be severed, such as the basal chord 10, which is the first chord encountered by catheter 20 just below the outflow tract, as seen in the ultrasound image pictured in FIG. 3A. (The tip of the catheter may be maneuvered, for example, using steering wires passed down its length.) In other embodiments, more than one chord will be cut. It may be preferable in some cases to sever pairs (symmetric or not) of chords, both of which are attached to the anterior leaflet, while in other cases attached to the posterior leaflet, and in still other cases chords from each leaflet may be severed. Selection of the chords to be severed depends upon the particular valve geometry disturbance encountered.

The instrument 25 may first grasp chord 10 to verify via cardiac imaging that the correct chord is being targeted. Cardiac imaging, such as, for example, ultrasound may also be employed to guide the catheter's insertion into the left ventricle 8 via the aorta. Such an approach takes advantage of the close proximity (less than 5 mm) of the chordal targets to the left ventricular outflow tract, where such a catheter would enter the ventricular cavity. The approach is also simplified because, under increased tension in the conditions being treated, the chords to be cut have no independent motion, and translate with the heart as a rigid body.

In an embodiment shown in FIG. 4A, the device is a hollow cylindrical catheter 20 with a notch 24 before its tip. The end of the opening is slanted at an angle of approximately at least 45° to provide a feature for holding the chord 10. The chord may also be held in place by advancing a thin wire 30 to the catheter tip, which is either deformed previously or by the end of the catheter to form a curve 26 over the chord. Other deformations in the wire suitable to grasp the chord 10, such as sharp to orthogonal bends or V-shapes, are possible. This figure presents only a preferred flexible hook to avoid any potential damage to encountered structures. Other shapes may maximize chances of capturing as opposed to displacing the chord.

The wire may be composed of a shape memory material such as super elastic nickel titanium alloy that assumes a predetermined shape automatically once the wire has been appropriately advanced proximate the chord. A sharp blade 28 shaped to fit into the notch is then advanced down the catheter to sever the chord. An alternative embodiment uses the same mechanism to stabilize the chord, but instead of a blade, standard optical fibers within the catheter apply high-intensity laser energy to sever the chord. In a further embodiment, radio-frequency energy, currently in routine use for therapeutic ablation of abnormal cardiac structures, is passed down the catheter or encircling wire 26 to disconnect the chord.

In an embodiment shown in FIG. 4B, the wire 26 is advanced beyond the open catheter tip 27 and used to grasp the chord 10. The wire 26 may again be composed of shape memory elastic material and have a pre-formed shape such as the hook illustrated. The chord is then withdrawn into the hollow end of the catheter, and a blade 28, laser fiber optics, or radiofrequency ablation wire advanced to sever the chord.

Figure 5A:
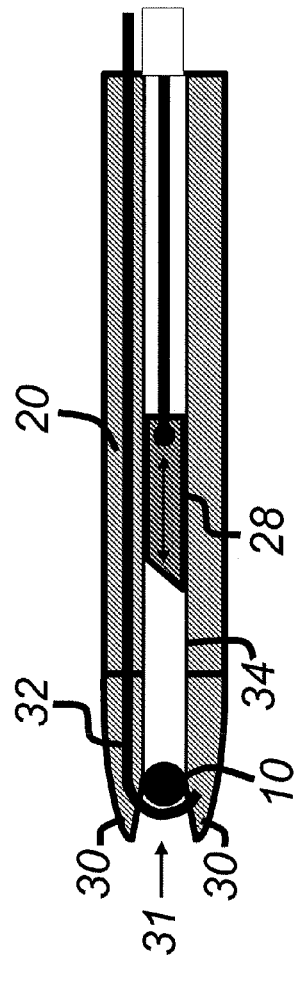
FIG. 5A is a schematic illustration of a side view of a chordal severing instrument employing forceps-like jaws.

With reference to FIG. 5A, an additional embodiment uses a forceps-like tool to grasp the chord 10. The end of the catheter 20 is armed with two movable jaws 30 that grab the chord. The catheter is advanced to maneuver the chord into the end of the slit 31 between the jaws. To stabilize the chord and allow it to be cut, a round or rectangular wire 32 is advanced down a side lumen of the catheter to wrap around the chord and firmly restrain it within the gap between the jaws. A sharp blade 28, laser fiber optics, or radiofrequency ablation wire is then advanced to sever the chord. The blade may be advanced through a slit 34 that continues from the main catheter into the jaws where the chord is held.

Figure 6A:
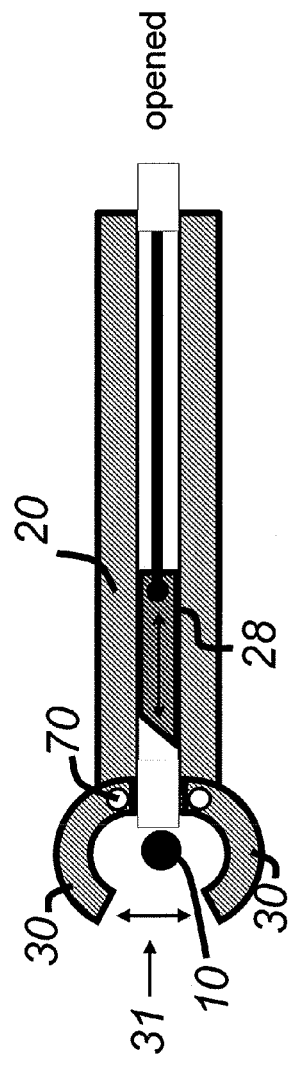
FIGS. 6A-6C are schematic illustrations of side views of chordal severing instruments employing pincer-like jaws.
Figure 6B:
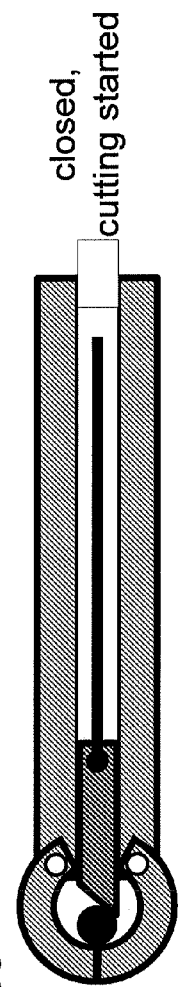
Figure 6C:
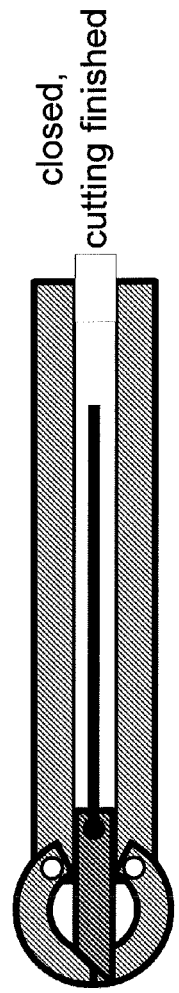

Another embodiment, shown in FIGS. 6A-6C, uses two curved pincer-like restraints to surround the chord and close over it in a circular fashion by pivoting on two hinges 70. A blade 28, fiber optic, or radiofrequency device is then advanced down the catheter between the restraints to pinion the chord and sever it. One experienced in the art will recognize that any of a class of forceps-like devices will be able to grasp the chord prior to its cutting.

The entire class of grasping and cutting devices described above may also be maneuvered with the embodiment shown in FIG. 7A. A stabilizing introducing catheter 18 is first advanced toward the left ventricular apex. The cutting catheter 20 is then passed through a port in the introducing catheter, either directly or through a directing arm 36 that may have an occlusive rubber seal. The introducing catheter 18 is stabilized by a curving contact element 19 extending beyond the catheter tip and shaped to maintain contact with the ventricular apex. The contact element 19 may actually comprise several elements composed of shape memory elastic material which, when extended from the catheter itself, form curving or tined contacting elements that may contact other portions of the interior of the cavity. The introducing catheter 18 may then be translated along this wire to position the cutting catheter 20 over the portion of the chord to be cut.

It is worth noting that the stabilizing mechanism described here is merely illustrative, as is its application to the positioning of the cutting instrument proximate the basal chord of the anterior mitral leaflet. The stabilizing mechanism is not limited to a wire or shape memory materials, nor is it limited to a single extendable contact element. For example, some embodiments may employ a plurality of stabilizing legs or telescoping extensions to contact inner left ventricle at numerous points around its circumference.

The cutting catheter may be steered toward the chord by taking advantage of the introducing catheter 18, as shown in FIG. 7B, in which the cutting catheter passes within a cylindrical collar 42 which is steered by positioning wires 43 to 46. A collar is not required, wires 43,46 may be directly connected to the cutting catheter 20. Pulling on 43 and releasing 44, for example, can point the catheter 20 toward the apex. These two wires may also be connected and spooled through the collar 42. Other catheter-steering mechanism known in the art are also deemed to be suitable for this purpose. For example, the cutting catheter may additionally be steered by some deflecting mechanism within the introducer catheter.

Guiding the entire process requires an imaging method capable of visualizing the basal chords and their deformation or displacement by the grabbing device prior to their being cut.

The chordae desired to be severed are readily recognized by ultrasound because they are thicker than the ones to the leaflet margins, as well as being virtually immobile in the patients being treated, and closest to the left ventricular outflow tract. Ultrasound imaging may be performed from the chest surface, esophagus, or within the heart, using an independent intracardiac echo (ICE) catheter (commercially available) within the adjacent right ventricular outflow tract, or an ultrasound transducer 40 within the left ventricle itself, built into the guiding catheter 18. Imaging the procedure from within the heart is made possible by the arrangement shown in FIG. 7A involving an introducing or guiding catheter 18 and a cutting catheter 20. This arrangement allows an imaging device 40 to be maneuvered within the guiding catheter to provide high-resolution images of the chordal structures during the procedure, while also displaying the mitral leaflets and regurgitant jet. The imaging device can be comprised of a two-dimensional ultrasound matrix array, a magnetic resonance coil, or fiber optics for transmitting and receiving near infrared energy that can pass around blood cells and provide a three-dimensional visual image, as embodied in U.S. Pat. No. 6,178,346, incorporated herein by reference. To produce a three-dimensional ultrasound image, a two-dimensional matrix array of piezoelectric crystals may be used, or a linear phased array may be rapidly rotated within the transducer housing 40 to produce a three-dimensional image.

Figures 8A, 8B:
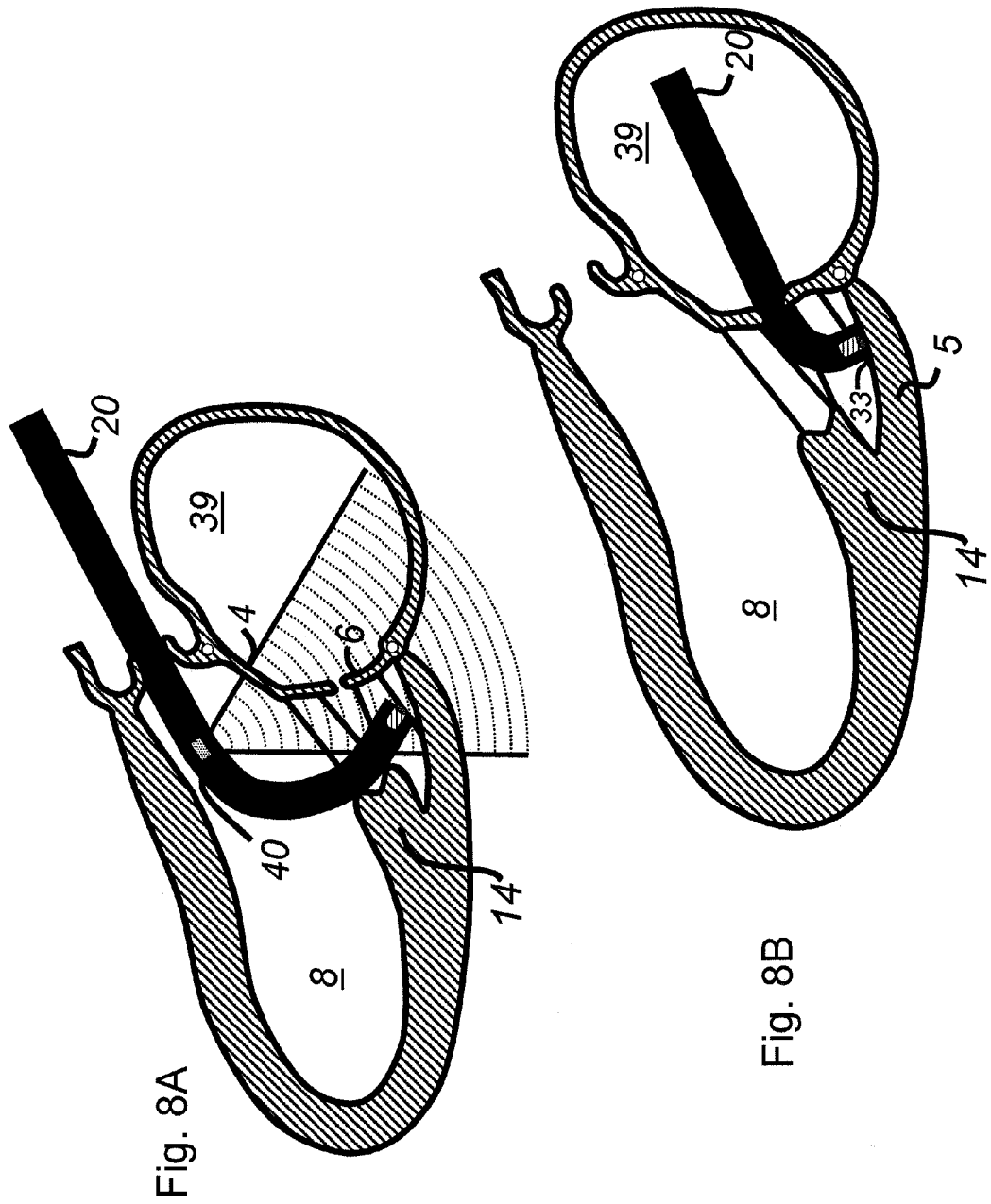
FIGS. 8A,8B are illustrations of cross-sectional views of a heart depicting various catheter insertion pathways.

Based on ultrasound imaging, basal chords to the posterior leaflet (6 in FIG. 8A) may also be seen to restrict leaflet motion prominently and merit attention. Leaflet motion may also be restricted by mural chords 33 connected to the posterior left ventricle wall 35 as opposed to the papillary muscle (14 in FIG. 8B). These chords to the posterior leaflet 6 can be approached by advancing an aortic catheter 20 retrograde into the left ventricle 8 and pre-formed or steered to curve downward between the two papillary muscles, possibly aided by shape memory elastic material. This design brings the grasping and cutting device of the catheter tip close to the chords 33 inserting on the posterior leaflet. An imaging device 40 may be maneuvered along the catheter to guide the process. Alternatively, a catheter may be inserted through the venous system and right atrium into the left atrium 39 across the atrial septum, as shown in FIG. 8B, and then maneuvered to engage and sever the posterior leaflet chords 33.

This approach was first verified with excised porcine mitral valves in a physiologic pulsatile flow simulator. It also effectively eliminated MR in seven sheep with functional MR caused acutely by inferior wall infarctions, and in seven sheep with chronic infarctions. No prolapse or deleterious effects on ventricular function have been noted with survival for a mean of seven months (as long as 11 months) in five sheep with chordal cutting of two following acute inferior infarction. A leading surgeon, Dr. Tirone David of Toronto General Hospital, has also practiced this method in nine patients without adverse effects and with demonstrable relief of mitral valve restriction.

With reference to FIGS. 9A-9D, a further embodiment of the present invention elongates selected chords as opposed to severing them alone. A splicing device 58 is inserted over the basal chord (thinner cylindrical structure). This device includes two semi-circular jaws 54 and a hinging mechanism 61. In the first step of the splicing process, the jaws are closed around the chord. One embodiment for doing this incorporates a set of inner and outer co-axial cables into the hinging mechanism 61, each cable mechanically linked to one jaw of the splicer in a design analogous to a door hinge. Rotating the cables toward each other closes the device around the chord. This rotation can be achieved through torque applied at the proximal end of the catheter, or by placing a compressed spring within the hinging mechanism 61 and then releasing a mechanical restraint placed on rotation of the cables. An alternative embodiment (shown in FIG. 9B) uses two control cables 63 and 65 rotated by two rods 62 and 64, respectively. Rotating the rods as shown closes the device around the chord; rotating in the opposite direction releases the device. A geared mechanism for rotating the control cables can achieve the same result.

Jaws 54 close three structures around the chord: two anchoring beads or nodes 56 and a radiofrequency ablation coil 62. The beads or nodes 56 are connected to elongated segments 60 of artificial chordal material such as, for example, Gortex (tetrafluoroethylene), which has been used extensively in mitral valve surgery. Other biocompatible, non-biodegradable materials may also be employed. These chordal lengths are housed within recesses 58 within the device casing. Once the jaws have closed around the basal chord, the separated halves of each bead on either side of the chord are permanently attached to one another (using heat, glue, or connecting pegs), and the basal chord segment between them severed using radiofrequency energy. Other severing means, such as those described above with respect to the cutting device, may be used as alternatives to the radiofrequency ablation.

The jaws of the device are then opened, releasing the final elongated chordal assembly shown in FIG. 9D, in which the artificial chordal lengths 60, connecting the two nodes, elongate the formerly shorter basal chord 10. The requisite length of chordal material may be calculated using three-dimensional ultrasound, which reconstructs the tethering distance between the papillary muscle tip and the anterior mitral annulus. The difference between this tethering length (increased in patients with ischemic MR) and an average normal value is used to calculate the necessary length of chordal elongation. Alternatively, this length may be determined empirically from nomograms established in patients with inferior myocardial infarction or global left ventricle dilatation, based on ventricular dimensions measured by echocardiography or other imaging methods such as MRI. (The nodes may be made of various materials, including plastics, ceramics, or titanium.)

Figure 9E:
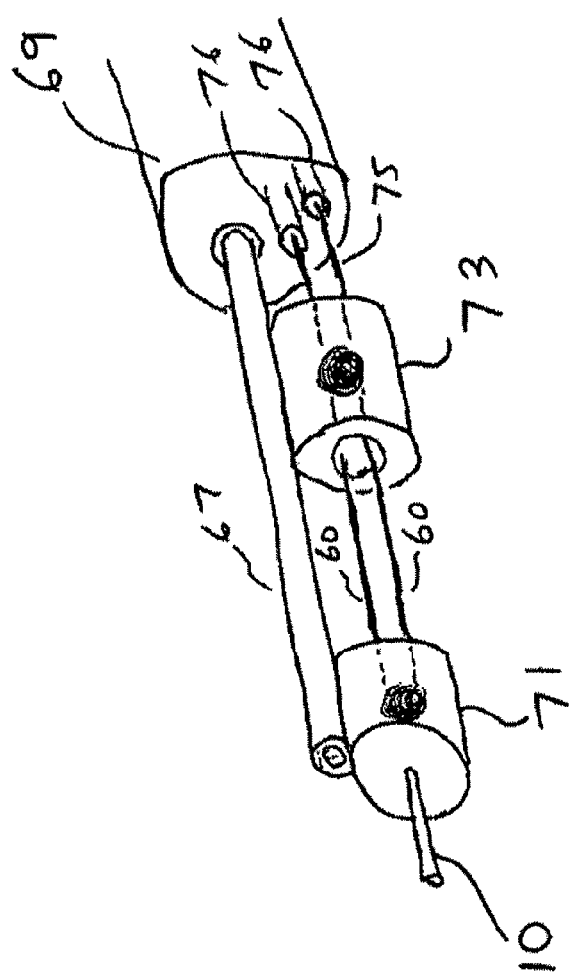
Figure 9G:
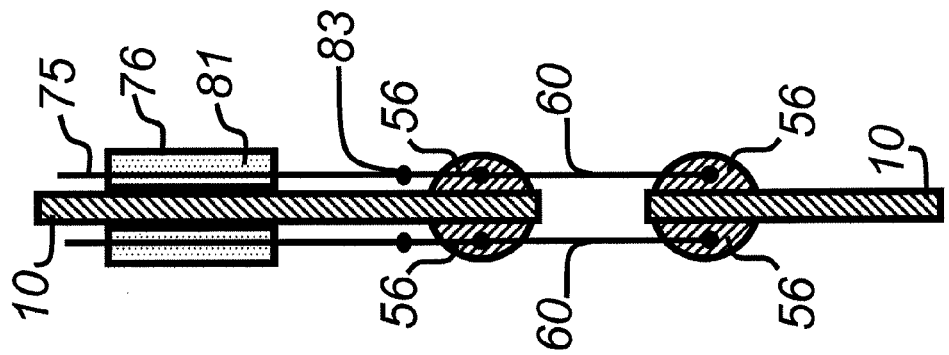
Figure 9F:
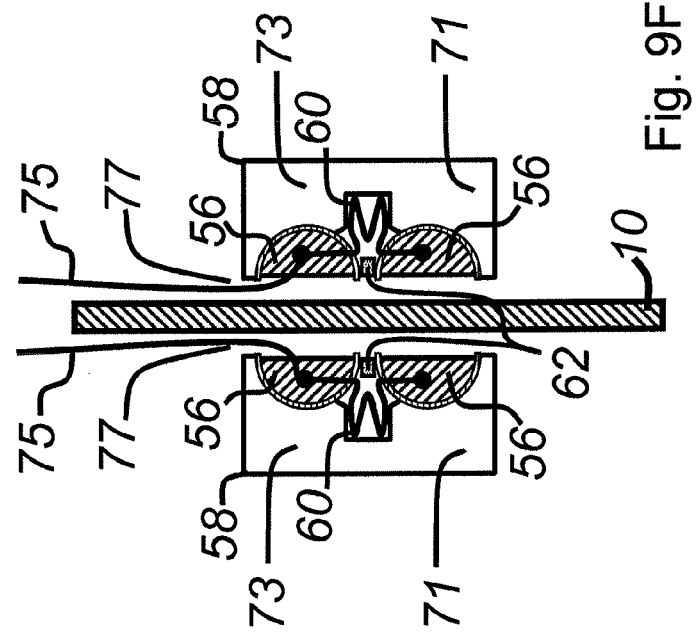

In some embodiments the chordal lengths 60 arespoolable during the elongation process to adjust the distance between the nodes 56. With reference to FIG. 9E, the housing carrying the nodes 56 is separated into two sections 71,73 that are extendable axially with respect to each other in order to place the nodes 56 along chord 10 wherever desired. The artificial chord length 60 connecting the nodes is enclosed in the housing. As the nodes 56 are separated via the housing sections 71,73, chordal material is drawn through the more proximal section 73 from a reserve 75 that extends along the axis of the main catheter through channels 76 that extend along that catheter 69. The valve being treated is observed to verify the desired configuration has been attained, and then the elongation/spooling is stopped. Finally, washers or some other locking mechanism is employed to affix the new chordal lengths into place and cut the reserve 75. This process is shown in greater detail in FIGS. 9F and 9G. With reference to FIG. 9F, the two displaceable sections of the housing 71,73 are shown to be separated, with an initial length of replacement chord 60 between them, and the continuation chordal material 75 extending through a channel in the proximal bead 56 and through a small groove 77 in the proximal face of housing portion 73. This allows the beads to be displaced relative to each other, and for the chordal material to increase in length between the two beads as it passes through a channel within the proximal bead 56. With reference to FIG. 9G, the reserve chordal length 75 extending down the main axis of the catheter is shown passing through channels 76. Once the desired chordal length is achieved, a pushing device 81 is passed down the length of these channels to lock the chord in place using a washer 83 that is advanced in front of the pushing device 81; the end of that device then disconnects the chordal segments between the beads from the reserve chord 75 using radiofrequency energy or other means of ablation. The beads are then separated by the chordal lengths 60 that have been adjusted and locked into position, as the housing is opened and the catheter withdrawn.

The present invention may be practiced as adjunct to other procedures for reducing the other end of the tethering mechanism that over-stretches the mitral leaflets, namely, the mitral annulus. This would provide a completely percutaneous approach to comprehensive repair of ischemic MR.

Other embodiments of all the above cutting or elongating devices may include within the catheter or device tip a mechanism for local imaging to guide approach and verify contact with the chord before it is altered. This may include an ultrasound-emitting piezoelectric crystal or existing technology for optical coherence tomography. Alternative embodiments involve depositing chemical compounds on the chord that increase its susceptibility to laser disruption by the methods described above. Further embodiments allow the chordal cutting or elongating devices to be inserted through the wall of the beating heart at the time of cardiac surgery, or percutaneously through a small incision in the diaphragm and pericardium, such as used for establishing a pericardial window.

Technology for minimally invasive fiber-optic video guidance of remotely manipulated tools (robotic surgery) may also be used to practice this method and invention in the beating heart without need for cardiopulmonary bypass. There may, however, be cases wherein the need to visualize the process may, ultimately, require initiating percutaneous cardiopulmonary bypass (e.g., with balloons in the aorta and veins leading to the right side of the heart) and then perfusing the heart cavities with clear fluid (e.g., saline or perfluorocarbons) to enable direct visual guidance with fiber optics.

Although illustrated for the particular case of inferior myocardial infarction with localized bulging of the LV wall, the same mitral valve deformation is present in patients with global LV dysfunction and dilatation, which should also be susceptible to the same therapeutic approach. This is particularly important in patients with global failure who are at greatest risk for open-heart surgery but could benefit the most from elimination of MR and its superimposed volume overload in a minimally invasive manner.

The device of this invention can also be applied in patients with rheumatic mitral stenosis to promote the effectiveness of other percutaneous treatments of rheumatic mitral stenosis, specifically percutaneous balloon mitral valvuloplasty, which until now has been limited in effectiveness in patients with restrictive chordal structures.

Finally, a similar approach can be applied using the catheter of the present invention advanced through the right atrium and tricuspid valve to remedy tricuspid valve tethering in patients with dilated or infarcted right ventricles. This would relieve the resulting tricuspid regurgitation that is deleterious to overall cardiac function and produces backflow of blood to the liver and extremities.

This or similar technology can also be used in other parts of the body for diagnostic or therapeutic purposes, for example, in laparoscopic surgery to hold and perform procedures on bile ducts, ureters, or other structures, as well as within the gastrointestinal tract itself.

While the foregoing specification has been described with regard to certain preferred embodiments, and many details have been set forth for the purpose of illustration, it will be apparent to those skilled in the art, that without departing from the spirit and scope of the invention, the invention may be subject to various modifications and additional embodiments, and that certain of the details described herein can be varied considerably without departing from the basic principles of the invention. Such modifications and additional embodiments are also intended to fall within the scope and spirit of the invention appended claims.

What is claimed is:

1. An apparatus for treating atrioventricular valve regurgitation, comprising:
    a cutting arrangement configured to sever at least one chord attaching an atrioventricular leaflet to an internal cardiac muscle;
    a positioning catheter configured to position the cutting arrangement proximate the at least one chord; and
    a grasping arrangement which is configured to at least partially constrain a movement of the at least one chord relative to the catheter,
    wherein the catheter comprises an opening provided within a side wall in which the grasping arrangement constrains the movement of the at least one chord and in which the cutting arrangement is configured to sever the at least one chord, wherein the grasping and cutting arrangements are provided in the catheter, wherein the grasping arrangement comprises a grasping member configured to slide along a longitudinal direction relative to an extension axis of the catheter, and wherein the grasping member comprises a wire.

2. The apparatus of claim 1, wherein the cutting instrument comprises a blade having a cutting edge width that is approximately the same size as a diameter of the at least one chord.

3. The apparatus of claim 1, wherein the cutting instrument comprises an optical fiber for delivering ablative laser energy.

4. The apparatus of claim 1, wherein the cutting instrument comprises a radiofrequency electrode.

5. The apparatus of claim 1, wherein the catheter has a curved end suitable to allow engagement of chords attached to a posterior leaflet.

6. The apparatus of claim 1, wherein the catheter includes a steerable tip.

7. The apparatus of claim 6, wherein the catheter further comprises coaxial steering wires for steering the catheter tip.

8. The apparatus of claim 1, wherein the opening comprises a notch in the catheter having a cross-sectional notch area greater than the cross-sectional area of the at least one chord.

9. The apparatus of claim 8, wherein the notch includes at least one protruding edge defining a portion of the notch for limiting motion of the at least one chord when positioned within the notch.

10. The apparatus of claim 1, further comprising an introducer catheter for advancing the positioning catheter toward the at least one chord.

11. The apparatus of claim 10, wherein the introducer catheter further comprises a directing arm through which the positioning catheter is maneuvered to the position proximate the at least one chord.

12. The apparatus of claim 10, wherein the introducer catheter further comprises a means for temporarily stabilizing the position of the introducer catheter within the LV.

13. The apparatus of claim 12, wherein the stabilization means comprises:
    one or more contact elements reversibly extendable from the introducer catheter so as to contact an internal surface of the heart cavity at one or more points.

14. The apparatus of claim 13, wherein the contact element is composed of, a shape memory elastic material that assumes the shape desired upon extension from the introducer catheter.

15. The apparatus of claim 10, further comprising an ultrasound transducer for imaging a region proximate the at least one chord located on the introducer catheter.

16. The apparatus of claim 10,
    wherein the positioning catheter protrudes from within the introducer catheter through an opening in the introducer catheter; and
    further comprising a plurality of positioning wires similarly disposed within and protruding from the introducer catheter, the positioning wires attached to the positioning catheter so as to enable steering of the end of the positioning catheter by selectively tensioning on one or more of the wires.

17. The apparatus of claim 10, wherein the introducer catheter further comprises an imaging device oriented so as to image a region near the mitral valve including the at least one chord.

18. The apparatus of claim 17, wherein the imaging device is comprised of a imager selected from the group consisting of a two-dimensional matrix array of piezoelectric crystals, a linear phased array and means for rotating the array within the catheter so as to produce a three-dimensional image, a magnetic resonance coil, and fiber optics for transmitting and receiving near infrared energy.

19. The apparatus of claim 1, wherein the cutting arrangement is further configured to sever at least one chord while the grasping arrangement is at least partially constraining a movement of the at least one chord.

20. The apparatus of claim 1, wherein a. distal end of the wire is curved.

21. The apparatus of claim 1, wherein a distal end of the wire comprises a hook-shaped portion.

22. The apparatus of claim 1, wherein the wire comprises a shape-memory material.

23. The apparatus of claim 1, wherein the grasping arrangement comprises at least one pincer member which is rotatably coupled to the catheter and which is configured to surround at least a portion of the at least one chord.

24. The apparatus of claim 1, wherein the grasping arrangement comprises at least two pincer members which are rotatably coupled to the catheter and which are configured to surround at least a portion of the at least one chord.

25. The apparatus of claim 1, further comprising a stabilizing arrangement configured to at least partially constrain a motion of the catheter relative to a location within a chamber of a heart and extend longitudinally past an edge of the catheter to contact a ventricle.

26. The apparatus of claim 25, wherein the stabilizing arrangement comprises an extendable member which is configured to contact the location within the chamber.

27. The apparatus of claim 26, wherein the stabilizing arrangement comprises a shape memory material.

28. The apparatus of claim 25, wherein the stabilizing arrangement is further configured to extend longitudinally to an apex of the ventricle with respect to an extension of the catheter.

29. The apparatus of claim 1, further comprising a second catheter configured to advance the positioning catheter toward the at least one chord.

30. The apparatus of claim 1, wherein the grasping arrangement retracts the at least one chord into the catheter.

31. The apparatus of claim 30, wherein the grasping arrangement retracts the at least one chord into the opening of the catheter, and wherein the cutting arrangement severs the at least one chord.

32. The apparatus of claim 1, wherein the cutting arrangement is further configured to sever the at least one chord only within the opening.

33. The apparatus of claim 1 wherein the grasping arrangement and the cutting arrangement are longitudinally coupled to one another.

34. The apparatus of claim 1, wherein the cutting arrangement is further configured to move only approximately in parallel with respect to a motion of the grasping arrangement to facilitate the severing of the at least one chord in the opening.

* * * * *